United States Patent [19]

Siczek et al.

[11] Patent Number: 5,078,142
[45] Date of Patent: Jan. 7, 1992

[54] PRECISION MAMMOGRAPHIC NEEDLE BIOPSY SYSTEM

[75] Inventors: Bernard W. Siczek, Boulder; Michael A. DePourbaix, Arvada; Michael Assa, Englewood, all of Colo.

[73] Assignee: Fischer Imaging Corporation, Denver, Colo.

[21] Appl. No.: 440,775

[22] Filed: Nov. 21, 1989

[51] Int. Cl.$^5$ ............................ A61B 5/05; A61B 6/04
[52] U.S. Cl. ................................ 128/653.1; 128/754; 378/37
[58] Field of Search .............. 128/916, 660.09, 653 R, 128/653 A; 73/618, 619, 620; 378/37, 208, 209; 606/130; 364/413.01; 269/323, 322, 324, 325

[56] References Cited

U.S. PATENT DOCUMENTS

| | | | |
|---|---|---|---|
| 2,707,662 | 5/1955 | Goldfield | 269/323 |
| 3,973,126 | 8/1976 | Redington | 378/37 |
| 4,485,819 | 12/1984 | Igi | 128/915 |
| 4,545,385 | 10/1985 | Pirschel | 128/915 |
| 4,613,122 | 9/1986 | Manabe | 378/209 |
| 4,618,973 | 10/1986 | Lasky | 378/37 |
| 4,750,487 | 6/1988 | Zanetti | 606/130 |
| 4,791,934 | 12/1988 | Brunnett | 128/653 R |
| 4,869,247 | 9/1989 | Howard | 606/130 |
| 4,875,478 | 10/1989 | Chen | 378/37 |

FOREIGN PATENT DOCUMENTS 78053931 6/1980 Sweden .

OTHER PUBLICATIONS

TRC Mammotest Diagnostic System for Breast Cancer, not dated, 6 pages.

TRC Mammotest System manufacturing drawings, not dated, 11 sheets.
TRC Mammotest Manual, not dated, 17 pages.

Primary Examiner—Kyle L. Howell
Assistant Examiner—Robert L. Nasser, Jr.
Attorney, Agent, or Firm—William E. Hein

[57] ABSTRACT

A precision mammographic needle biopsy system in which a patient having a suspected non-palpable lesion of the breast lies on a table having a breast aperture therein through which the patient's breast pendulantly protrudes includes a compression paddle for selectively compressing the breast against an X-ray film holder to firmly hold the breast in a suitable projection; a radially pivoting X-ray arm arranged to direct an X-ray beam in horizontal alignment with the patient's breast onto an X-ray film; a radially pivoting X-ray film holder arm supporting both the X-ray film holder and a puncture instrument holding a biopsy needle having adjustable azimuth angle, elevation angle, and insertion depth parameters; and a computer-digitizer console including a cursor and having a light box digitizer view area for viewing and digitizing a point of interest depicted in two stereoscopic X-ray images of the patient's breast, a computer for analyzing the relative positions of the point of interest depicted on the two stereoscopic X-ray images with reference to a pair of reference marks projected onto each of the images and for determining the location in 3-dimensional space of the point of interest specified by the azimuth angle, elevation angle, and insertion depth parameters of the biopsy needle, and a visual display for displaying these parameters to the operator.

16 Claims, 9 Drawing Sheets

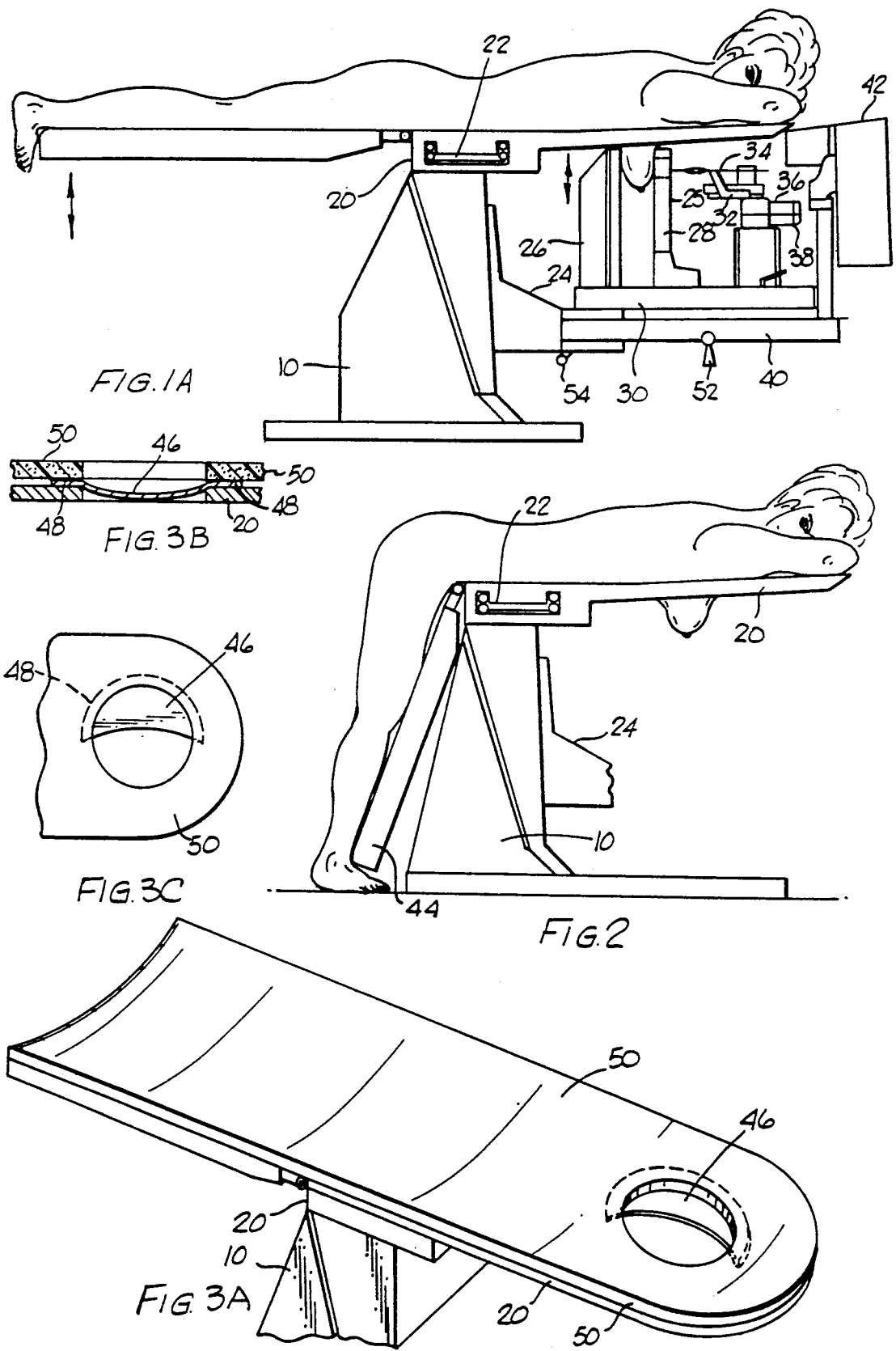

PRECISION MAMMOGRAPHIC NEEDLE BIOPSY SYSTEM

BACKGROUND AND SUMMARY OF THE INVENTION

This invention relates generally to medical mammography systems that are designed to detect non-palpable lesions of the female breast. More particularly, this invention is directed to an advanced mammographic needle biopsy system for quickly and easily localizing difficult non-palpable lesions to obtain cell or tissue samples. A surgical biopsy performed because a mammography shows a suspected malignant lesion leads, in many cases, to extensive disfiguring surgery of the breast. This occurs despite the fact that the pathology conducted after the surgery in most cases reveals that there is no sign of cancer. Surgical biopsies of this sort are costly, involved, and tie up surgical resources for which there is often a greater need elsewhere.

A known diagnostic system for detecting breast cancer is the TRC Mammotest system manufactured by Tekniska Roontgencentralen AB of Sweden. This prior art system functions in accordance with the principle that a tumor which is photographed by X-ray from separate angles relative to the normal of the film plane is projected in different positions on the film. The X-Y coordinates for these projections can then be measured in relation to a pair of X-Y coordinate scales that are projected onto the film as the X-rays are being taken. The position of the tumor can be calculated using known geometric relationships. A puncture instrument is then used to precisely insert a biopsy needle into the breast until the tip of the needle is located at the center of the tumor.

During operation of the prior art TRC Mammotest system, the patient is in a recumbent prone position on a table that can be raised or lowered, the breast protruding pendulant through an aperture at the cranial end of the table. A compression plate holds the breast firmly in a suitable projection against an X-ray film holder. It is advantageous in several respects that the patient be in a prone position during the examination, rather than standing or sitting, as is the case in conventional mammography screening systems. First, this position, in which the breast is pendulant, makes positioning the breast much easier. In addition, the prone position allows even small breasts to be compressed satisfactorily for mammography and subsequent biopsy. As the patient should not be allowed to move the breast during the procedure, this condition can be achieved much easier if she is in a recumbent prone position. Finally, it is also desirable from a safety point of view that the procedure be conducted while the patient is in a prone position, as there is always a risk of fainting in any type of surgical examination.

Two X-ray views of the compressed breast are conventionally taken, at angles of +15 degrees and −15 degrees to the normal through the plane of the film. This technique results in two different projections of the lesion in relation to a pair of radio opaque orthogonal coordinate scales that are engraved into the compression plate and are thus projected onto the X-ray film. A point of interest appearing on the two X-ray views is selected, and a manual measurement of the X and Y coordinates of the point is made with reference to the pair of orthogonal coordinate scales appearing on the two X-ray views. These manually measured X and Y coordinates are then manually entered into a calculator for calculation of the composite coordinates used for manually setting the puncture instrument. The puncture instrument, fitted with a desired biopsy needle, is then placed in a position agreeing with the calculated composite coordinates of the point of interest and the needle is inserted into the breast until the tip of the needle reaches the point of interest. As a check, and to provide a documented record that the biopsy sample has been taken from the intended point of interest within the breast, two additional X-ray views are taken while the needle is inserted in the breast. The biopsy needle is then withdrawn and the sampling terminated.

The prior art system described above is disadvantageous in several respects. For instance, the table on which the patient lies during the procedure, while it can be lowered to permit mounting by the patient and then raised to give the doctor room beneath the table to conduct the procedure, is nevertheless fixed in a horizontal position. Since the table does not fold and cannot be inclined from its fixed horizontal position, it is oftentimes difficult for patients to mount the table, even in its lowered position. It is also a disadvantage that the aperture through which the breast under examination depends is of a fixed size in that it is therefore difficult to accommodate a wide range of women's sizes. In addition, the table of the prior art system is strictly flat, thereby preventing examination of a patient's breast tissue that lies very near the chest wall. Also, accuracy and speed of the prior art system are impaired as a result of the required manual measurement, with reference to the projected coordinate scales, of the X and Y coordinates of the point of interest displayed on the two X-ray views. Moreover, the X and Y coordinate scales that are projected onto the film as the X-rays are being taken result in obscuring a portion of the breast tissue that would otherwise be clearly shown in the X-ray views.

It is therefore an object of the present invention to provide an improved mammographic needle biopsy system in which the table on which the patient lies during the examination procedure has a hinged foot section that permits easy mounting and dismounting by the patient.

It is a further object of the present invention to provide an improved mammographic needle biopsy system in which the table on which the patient lies during the examination procedure is concave with respect to its longitudinal axis to permit examination of the patient's breast tissue that is adjacent the chest wall.

It is a further object of the present invention to provide an improved mammographic needle biopsy system in which a breast aperture in the surface of the table on which the patient lies during the examination procedure includes an adjustable diaphragm for partially covering a selected portion of the breast aperture to thereby permit exposure of only the breast under examination.

It is a further object of the present invention to provide an improved mammographic needle biopsy system in which the patient's breast is held in a compressed position in a spaced apart relationship between an X-ray film and an X-ray beam source to result in magnification of X-ray images of the breast.

It is a further object of the present invention to provide an improved mammographic needle biopsy system in which radially pivoting film and X-ray arms are supported by means of tapered roller bearings and in which those arms are locked in a desired position by means of wedge-shaped mating locking parts to prevent undesirable movement of the arms and resultant loss of overall accuracy of the measurements made by the system.

It is a further object of the present invention to provide an improved mammographic needle biopsy system in which a biopsy needle is positioned in the same plane as that containing the horizontal pivoting axis of a puncture instrument holding the biopsy needle.

It is a further object of the present invention to provide an improved mammographic needle biopsy system in which a spring-loaded biopsy gun is employed for rapid insertion of a biopsy needle to a specific point of interest within the patient's breast.

It is a further object of the present invention to provide an improved mammographic needle biopsy system in which a digitizer is employed to digitize the location of a point of interest within the patient's breast that appears on a pair of stereo X-rays that do not have coordinate scales depicted thereon and in which the vertical angle, horizontal angle, and insertion depth parameters defining that point of interest are automatically calculated and displayed to the user.

It is a further object of the present invention to provide an improved mammographic needle biopsy system in which micrometers and a depth stop controlling a puncture instrument for adjusting the vertical angle, horizontal angle, and insertion depth parameters of a biopsy needle held by the puncture instrument include position encoders and motorized means for automatically setting those parameters in response to a digitized determination of the values of those parameters associated with a specific point of interest within the patient's breast.

BRIEF DESCRIPTION OF THE DRAWINGS

FIG. 1A is a pictorial diagram illustrating a portion of a mammographic needle biopsy system constructed in accordance with the present invention.

FIG. 2 is a pictorial diagram illustrating the patient table of the mammographic needle biopsy system of FIG. 1 as being hinged to facilitate mounting and dismounting by the patient.

FIG. 3A is a pictorial diagram illustrating the concave surface of the patient table of FIGS. 1 and 2, as well as a breast aperture in the patient table and an associated diaphragm cover therefor.

FIG. 3B is a cross sectional view of a portion of the patient table of FIG. 3A illustrating the positioning of the diaphragm cover between the table base and a padded cover therefor.

FIG. 3C is a plan view of the portion of the patient table of FIG. 3A that includes the breast aperture and diaphragm cover.

DETAILED DESCRIPTION OF THE INVENTION

Figure 1B:
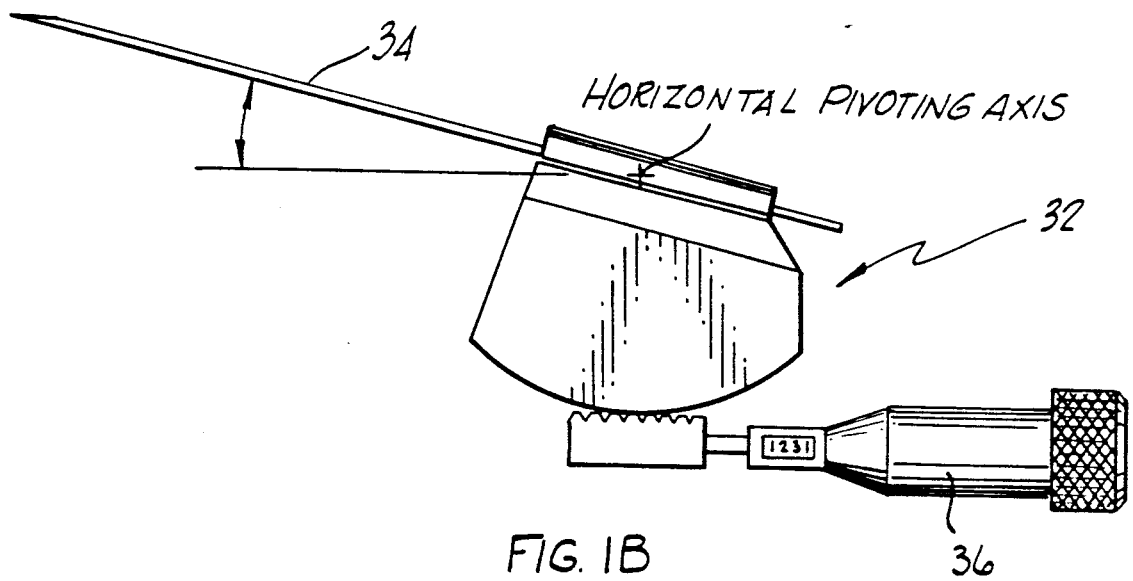
FIG. 1B is a pictorial diagram illustrating an embodiment of puncture instrument 32 of FIG. 1A in which needle 34 is mounted so as to lie in a plane common with the plane in which the horizontal pivoting axis of needle 34 lies.

Referring now to the pictorial diagram of FIG. 1A, there is shown a portion of a mammographic needle biopsy system constructed in accordance with the present invention that comprises a pedestal base 10, a patient table 20, a film holder arm 30, and an X-ray arm 40. Pedestal base 10 houses conventional electromechanical devices for selectively raising and lowering patient table 20, film holder arm 30, and X-ray arm 40. Alternatively, patient table 20, film holder arm 30, and X-ray arm 40 may be arranged for adjustable inclination from the horizontal to permit medical personnel more working space in which to maneuver film holder arm 30 and X-ray arm 40 beneath patient table 20. The controls for initiating these various mechanical functions are conveniently located on a control handle 22 alongside patient table 20. Film holder arm 30 is supported at one end thereof by an arm carrier 24 and is arranged to pivot radially in a horizontal plane about its connection point to arm carrier 24. X-ray arm 40 is also supported at one end thereof by arm carrier 24 below and in vertical alignment with film holder arm 30 and is also arranged to pivot radially in a horizontal plane about its connection point to arm carrier 24. Primary positions of the film holder arm 30 and X-ray arm 40 are represented by radial movement of plus or minus 90 degrees from the longitudinal axis of patient table 20. Primary detents are provided to lock film holder arm 30 and X-ray arm 40 at their −90, −45, 0, +45, and +90 degree primary positions. Secondary detents are provided to lock the X-ray arm 40 at positions which represent radial motion of plus or minus 15 degrees from each primary position for stereoscopic imaging, as well as at the 0 degree position for general mammography. Independent or simultaneous radial movement of both the film holder arm 30 and the X-ray arm 40 is controlled by locking handles 52 and 54 located beneath X-ray arm 40. A film holder 26 is mounted on top of film holder arm 30 proximate the pivot point thereof.

Figure 6:
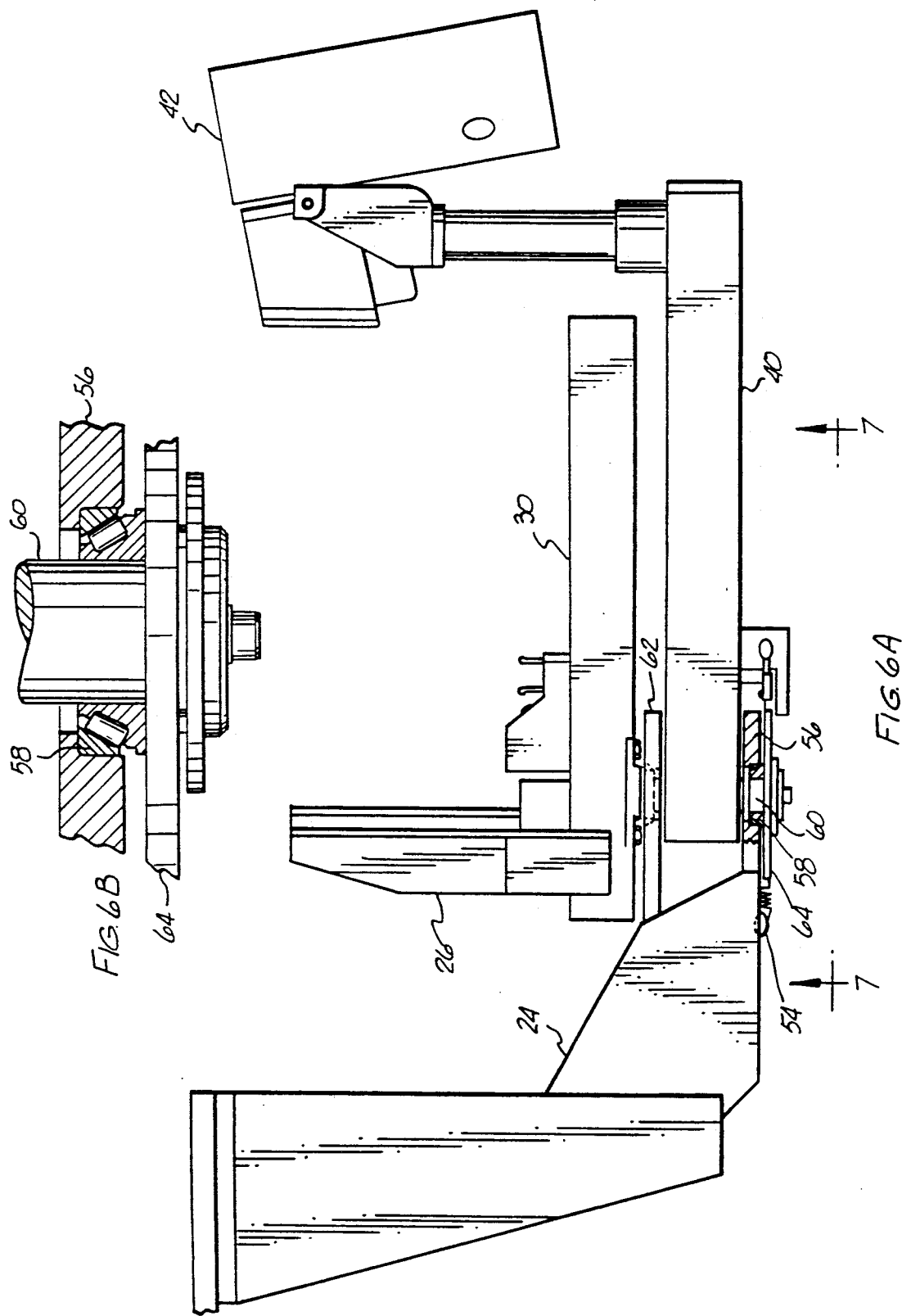
FIG. 6A is a pictorial diagram illustrating the support and locking mechanism for a film holder arm and an X-ray arm that are part of the portion of the mammographic needle biopsy system illustrated in FIG. 1.
FIG. 6B is a cross sectional diagram illustrating the details of a tapered bearing support system for the X-ray arm of FIG. 6A.
Figure 7:
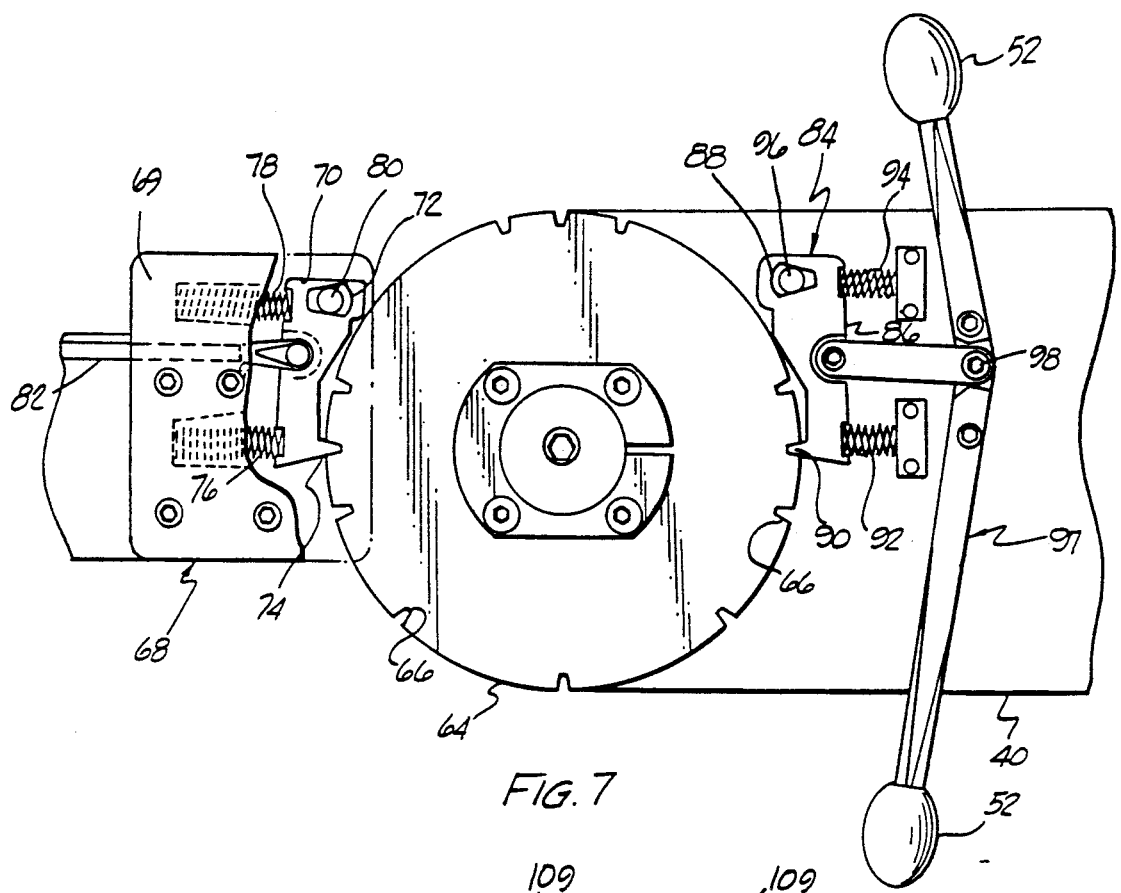
FIG. 7 is a detailed mechanical diagram of the locking mechanism for the film holder and X-ray arms illustrated in FIGS. 1 and 6A.

Referring now to the more detailed mechanical diagrams of FIGS. 6A-B and 7, there is shown a support plate 56 attached to arm carrier 24. A tapered roller bearing assembly 58 resides within support plate 56 and receives a shaft 60 on which X-ray arm 40 is supported for radial motion. A similar tapered roller bearing assembly resides within a support plate 62 and also receives shaft 60 on which film holder arm 30 is supported for radial motion above X-ray arm 40. The use of tapered roller bearings results in substantial elimination of undesirable backlash and play in the support of film holder arm 30 and X-ray arm 40 and thereby increases the overall accuracy of the mammographic needle biopsy system.

A circular detent plate 64 includes a number of wedge-shaped detents 66 spaced around its periphery to lock the film holder arm 30 and X-ray arm 40 into the positions referenced above. An arm assembly lock 68 serves to lock radial motion in concert of film holder arm 30 and X-ray arm 40. Arm assembly lock 68 includes a stationary plate 69 mounted to the underside of arm carrier 24. A locking dog 70 includes an elongated wedge-shaped opening 72 at a pivot end thereof and a lock tab 74 at the other end thereof. Lock tab 74 is wedge-shaped to provide precise mating engagement with wedge-shaped detents 66 around the periphery of circular detent plate 64. A spring 76 urges wedge-shaped lock tab 74 into complete engagement with a selected one of wedge-shaped detents 66. A spring 78 urges the sides of elongated wedge-shaped opening 72 at the pivot end of locking dog 70 into engagement with a circular pivot pin 80 mounted on stationary plate 69. A lever 82, hingedly connected to locking dog 70, is controlled by handle 54 to move wedge-shaped lock tab 74 out of engagement with one of the wedge-shaped detents 66 to permit radial motion in concert of film holder arm 30 and X-ray arm 40.

An X-ray arm lock 84 is mounted to the underside of X-ray arm 40 and diametrically positioned with respect to arm assembly lock 68. A locking dog 86, similar in shape to locking dog 70, includes an elongated wedge-shaped opening 88 at a pivot end thereof and a lock tab 90 at the other end thereof. Lock tab 90 is wedge-shaped to provide precise mating engagement with wedge-shaped detents 66 spaced around the periphery of circular detent plate 64. A spring 92 urges wedge-shaped lock tab 90 into complete engagement with a selected one of wedge-shaped detents 66. A spring 94 urges the sides of elongated wedge-shaped opening 88 at the pivot end of locking dog 86 into engagement with a circular pivot pin 96 mounted on the underside of X-ray arm 40. A lever 97 is hingedly connected at pivot point 98 to the the underside of X-ray arm 40 and is controlled by either of handles 52 that extend outwardly of the sides of X-ray arm 40 to move wedge-shaped lock tab 90 out of engagement with one of the wedge-shaped detents 66 to permit radial motion of X-ray arm 40 independent of film holder arm 30. The use of wedge-shaped detents 66 on circular detent plate 64, together with precisely mating wedge-shaped lock tabs 74 and 90 that engage therewith results in backlash free locking of film holder arm 30 and X-ray arm 40 to significantly increase the overall accuracy of the mammographic needle biopsy system.

A compression paddle 28 is slidably mounted outwardly from film holder 26 on top of film holder arm 30 and is employed to compress the patient's pendulant breast protruding through an aperture in patient table 20 against film holder 26 preparatory to taking stereoscopic X-ray views thereof. Sliding motion of compression paddle 28 may be controlled manually or by a footswitch coupled to a conventional motorized mechanism. An automatic compression control, which adjustably limits the amount of breast compression, may be provided. A compression plate 25 is positioned in front of film holder 26 and may be spaced away therefrom. Compression paddle 28 is operative for compressing the patient's breast under examination against compression plate 25. By so compressing the patient's breast in a spaced position in front of film holder 26, the X-ray image of the patient's breast is magnified.

A puncture instrument 32 for retaining a biopsy needle 34 is mounted on top of film holder arm 30 outwardly from compression paddle 28. Puncture instrument 32 is mounted to film holder arm 30 in a conventional manner by means of horizontal and vertical stages whose angular positioning is controlled by a pair of precision micrometers 36 and 38. A depth scale and depth stopper forming part of puncture instrument 32 control the depth to which biopsy needle 34 is inserted into the compressed pendulant breast of the patient during an examination procedure. Horizontal angle, vertical angle, and insertion depth parameters that define the point of interest within the patient's breast to which biopsy needle 34 is to be inserted are conventionally set into micrometers 36 and 38 and into the depth stopper manually by the operator. However, micrometers 36 and 38, as well as the depth stopper, may include known position encoders and motorized means for automatically setting the proper angle and depth parameter values into those devices, thereby eliminating the opportunity for human error. Biopsy needle 34 is conventionally manually inserted into the patient's breast following setting of the proper angle and depth parameter values. However, as the tip of biopsy needle 34 approaches tumorous tissue within the breast, that tissue may tend to move as the needle slowly approaches. In order to avoid this undesirable result, a conventional spring-loaded biopsy gun may be retained in puncture instrument 32 for rapidly inserting a biopsy needle to a specific point of interest within the patient's breast. The spring-loaded biopsy gun may comprise, for example, the BIOPTY gun marketed by the Bard Urological Division of C. R. Bard, Inc, Covington, Ga.

A conventional X-ray tube assembly is mounted on top of X-ray arm 40 at the outward end thereof and is arranged to direct an X-ray beam in horizontal alignment with the patient's compressed pendulant breast onto an X-ray film retained within X-ray film holder 26.

Referring now to the pictorial diagram of FIG. 2, patient table 20 includes a hinged foot portion 44 illustrated in a lowered position to facilitate mounting and dismounting by the patient. Once the patient has positioned herself as shown in FIG. 2, the foot portion of patient table 20 is raised to the horizontal position illustrated in FIG. 1A. Similarly, the foot portion 44 of patient table 20 is lowered to the position shown in FIG. 2 following the examination procedure to facilitate dismounting by the patient. Control of the position of foot portion 44 of patient table 20 may be accomplished via any of a number of conventional manual or motorized mechanisms.

Referring now to FIG. 3A, there is shown the patient table 20 of FIGS. 1A and 2 formed to be concave in shape along the longitudinal axis thereof to permit examination of the patient's breast tissue that is adjacent the chest wall. A pad 50 covers table 20 to provide a comfortable surface on which to lie. Also illustrated in FIG. 3A is a breast aperture through which one of the patient's breasts is permitted to pendulantly protrude. Alternatively, table 20 may have a generally flat surface on which the patient lies, but include a dish-shaped area around the breast aperture to permit examination of the patient's breast tissue that is very near her chest wall. In order to accommodate patients of varying size, a diaphragm cover 46 is provided that may be rotated within the breast aperture to selectively cover a desired portion thereof so that only a selected one of the patient's breasts protrudes through the breast aperture. Diaphragm cover 46 is illustrated in more detail in FIGS. 3B and 3C to include a flange 48 that secures diaphragm cover 46 in place over the breast aperture in patient table 20. Flange 48 is retained between table 20 and pad 50.

Figure 4:
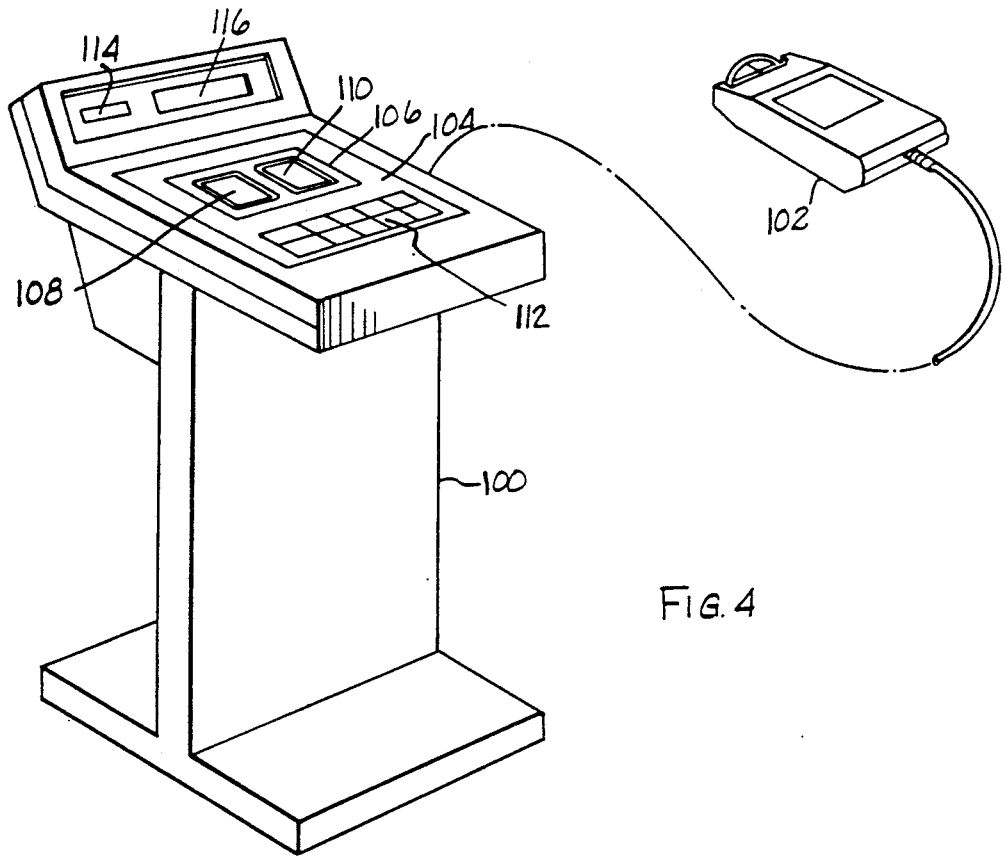
FIG. 4 is a pictorial diagram of a computer-digitizer console and cursor that are employed with the portion of the mammographic needle biopsy system illustrated in FIG. 1.
Figure 9:
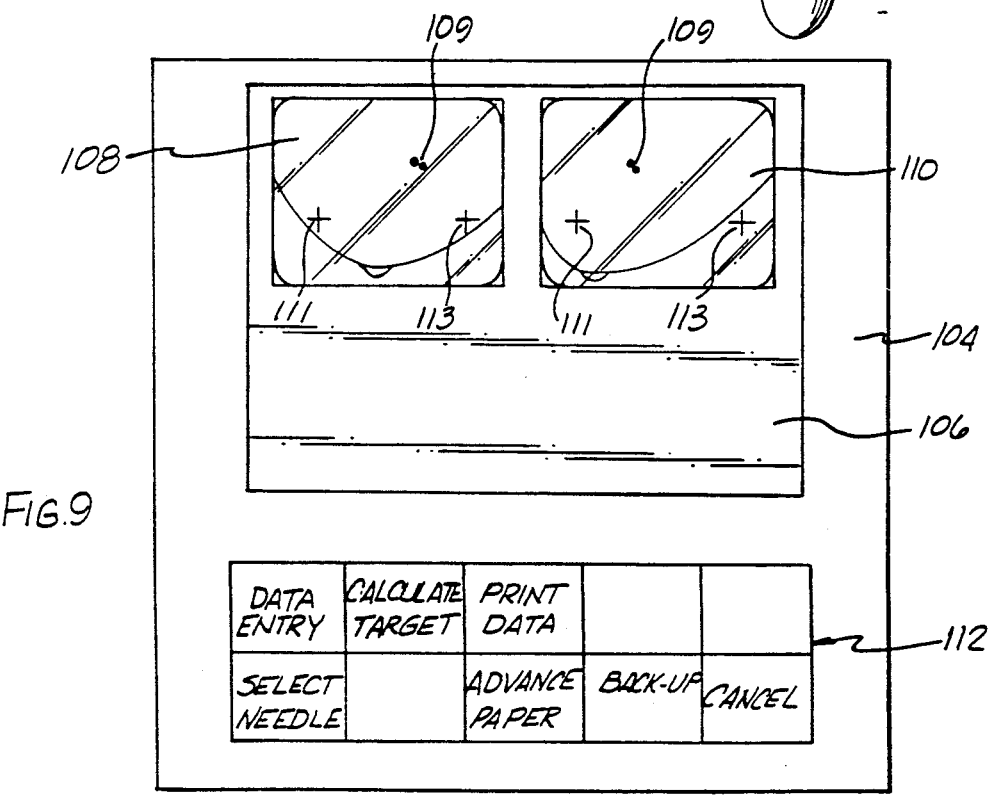
FIG. 9 is a diagram illustrating the layout of the platen area of the computer-digitizer console of FIG. 4.
Figure 8A:
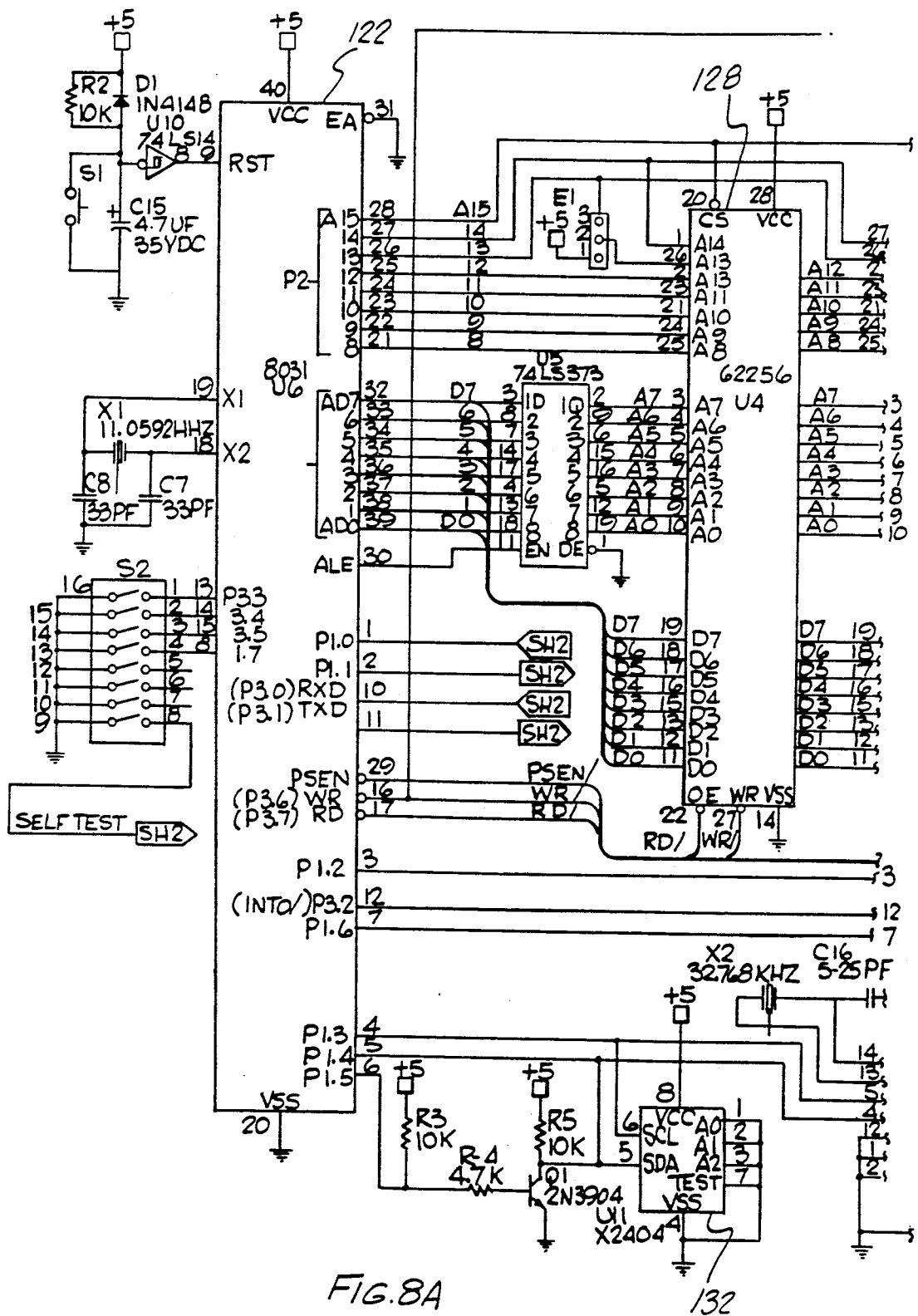
FIGS. 8A-D are a detailed schematic diagram of circuity employed in the computer-digitizer console and cursor illustrated in the block diagram of FIG. 5.
Figure 8B:
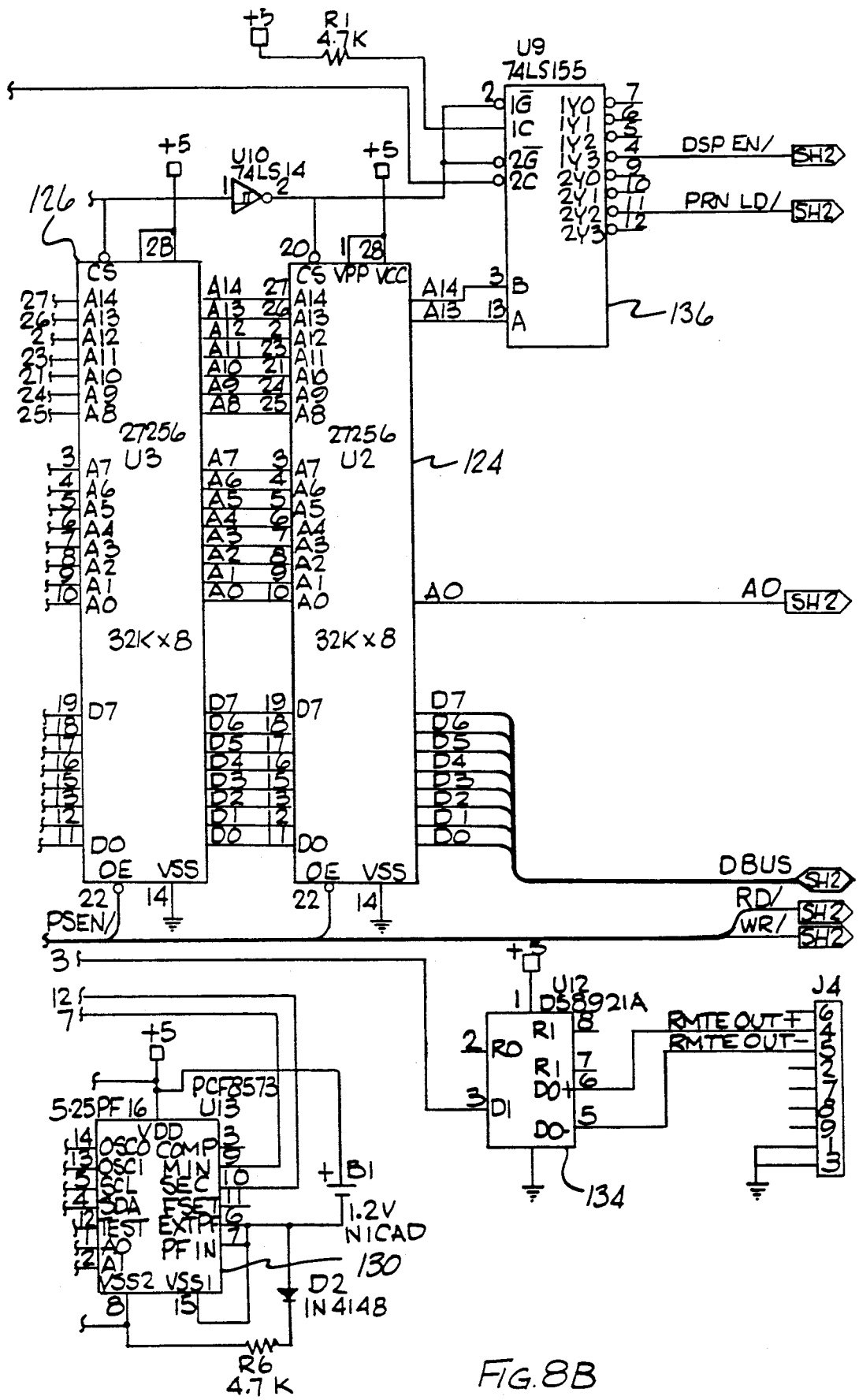
Figure 8C:
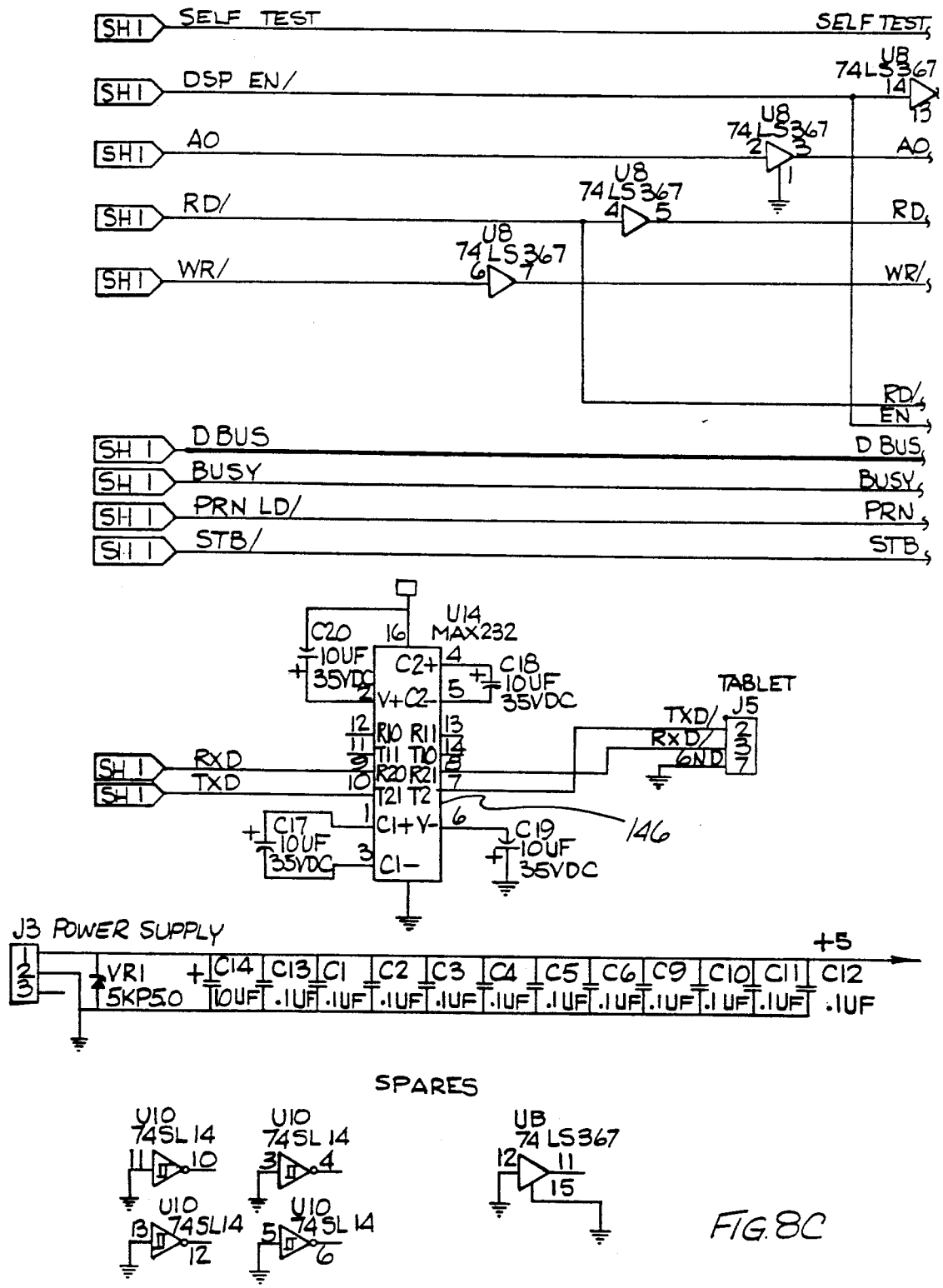
Figure 8D:
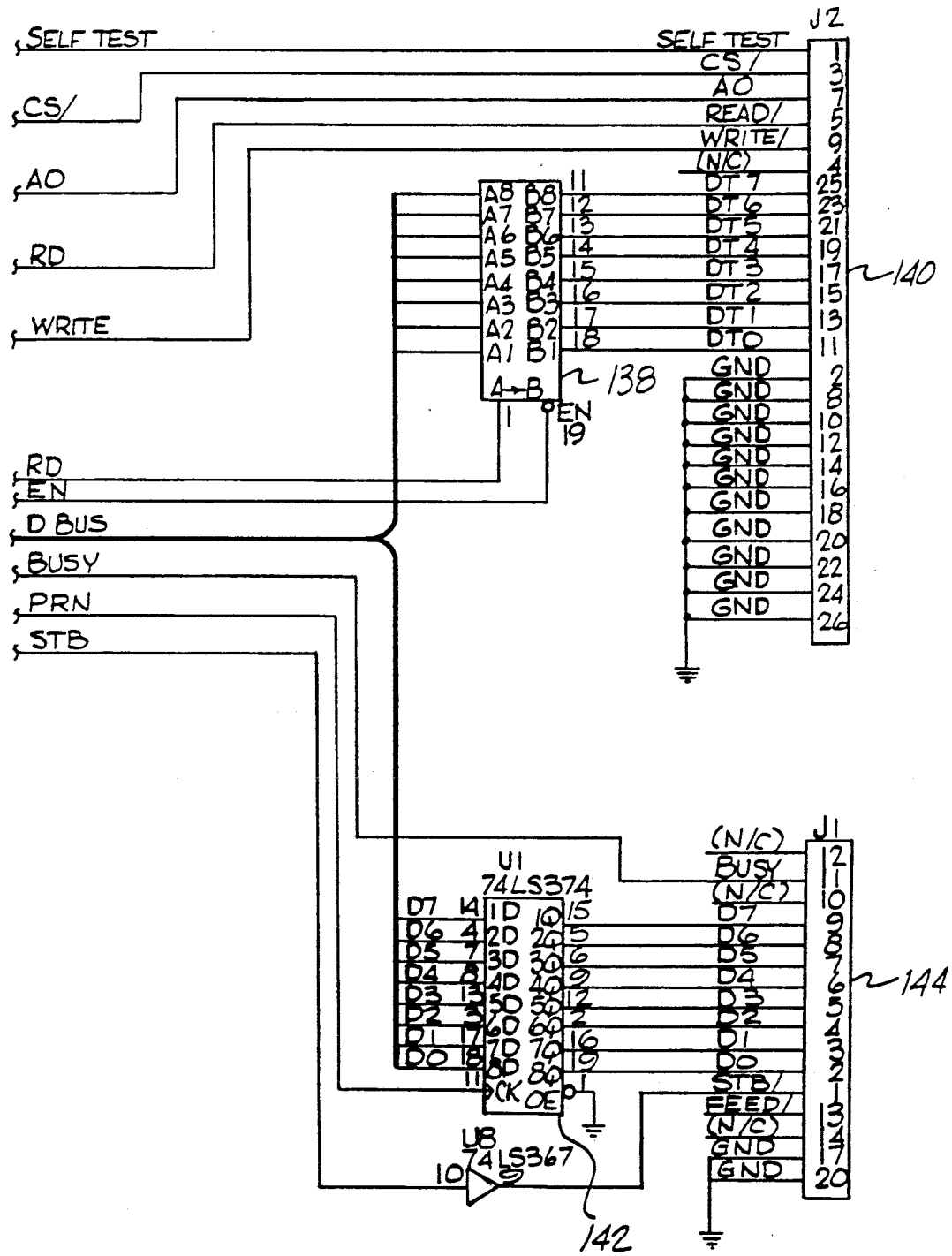

Referring now to FIGS. 4 and 9, there is shown a computer-digitizer console 100 and cursor 102 that are employed to automatically compile information from two stereoscopic X-ray images of the patient's breast. Computer-digitizer console 100 includes a platen area 104 having a light box viewing area 106 over which two stereoscopic X-ray images 108, 110 are positioned for viewing and digitizing. Platen area 104 also includes a function control area 112 for selecting certain functions to be performed by computer-digitizer console 100. Computer-digitizer console 100 includes a printer 114 for providing a printed record of the vertical angle, horizontal angle, and depth parameters of a point of interest 109 depicted on the two stereoscopic X-ray images 108, 110 and an alphanumeric information display 116 for visually displaying alphanumeric function information selected from function control area 112 of platen area 104, as well as other alphanumeric messages. Cursor 102 is employed on platen area 104 and comprises a one-button mouse with crosshairs that enables the user to select specific functions specified within function control area 112 of platen area 104 and to digitize a point of interest 109 depicted on the two stereoscopic X-ray images 108, 110 of the patient's breast.

Computer-digitizer console 100 is operative for analyzing the relative positions of two stereoscopic images 108, 110 taken from two angles and for determining the location in 3-dimensional space of a point of interest 109 shown on the two stereoscopic images 108, 110. In addition, computer-digitizer console 100 is operative for automatically calculating the vertical angle, horizontal angle, and depth of insertion parameters necessary to direct a biopsy needle 34 retained by puncture instrument 32 of FIG. 1A to the point of interest 109 within the patient's breast. The calculations which are made are based on straightforward analytical geometry, and the routines and subroutines of instructions that are executed by computer-digitizer console 100 to perform these calculations are detailed in the firmware listing that follows this specification.

In order to obtain the two stereoscopic images required of the patient's breast, two separate X-rays are taken of the breast from angles of +15 degrees and −15 relative to the normal of the film plane. As a result, a point of interest 109, such as a tumor, shows up in two different positions on each of the two X-ray images 108, 110. Due to the geometry of the present mammographic needle biopsy system, only the X coordinate of the point of interest 109 changes. The Y coordinate remains the same in both X-ray images 108, 110. Thus, when evaluating the two stereoscopic images 108, 110, a point of interest 109 located in the first image 108 is always in the exact vertical plane in the second image 110. The plus and minus 15 degree stereo angle causes the apparent position of an object to translate only in the horizontal plane, never in the vertical plane. A straightedge placed between a pair of projected reference marks 111, 113 on each X-ray image 108, 110 easily defines the horizontal plane to assist in film evaluation. These reference marks are projected with a parallax error in both the X and Y directions because they are not in direct contact with the film but are spaced approximately 10 millimeters away from the film. This parallax error is corrected by way of correction routines executed by computer-digitizer console 100.

Since the geometry of the present mammographic needle biopsy system is known, it is possible to mathematically reconstruct the location of the 3-dimensional breast of the patient with respect to the center of the puncture instrument 32 of FIG. 1A by observing where the breast is projected in the two X-ray stereoscopic images 108, 110. To accurately locate a point of interest 109 depicted on the two stereoscopic X-ray images 108, 110 of the breast, a high resolution digitizer is employed as part of computer-digitizer console 100. Point of interest 109 is located with respect to the absolute reference provided by the two projected reference marks 111, 113 located on each of the two stereoscopic X-ray images 108, 110. The general mathematical technique for aligning an image with a digitizer is to develop a transformation matrix that can accept an input vector defined by the raw X and Y coordinates of the point of interest as determined by the digitizer. These raw coordinates are then transformed mathematically to an output vector defined in terms of X and Y coordinates relative to the system coordinates 0,0 of the two stereoscopic X-ray images 108, 110. The transformation matrix is the result of successively applying translate, rotate, and scale operators to an identity matrix.

The first step in building this transformation matrix is to use knowledge of the location, relative to the film and X-ray source, of the two registration marks 111, 113 projected onto each of the two stereoscopic X-ray images 108, 110. This sets a reference point for the digitizer. The parallax error in the Y direction is constant since both the left and right registration marks 111, 113 have the same Y coordinates and both positions of the X-ray source are at Y=0. Therefore, the Y coordinate of a line between the two reference marks 111, 113 as they appear on the two stereoscopic X-ray images 108, 110 is constant. Next, using standard principles of analytical geometry, the parallax error in the X direction is calculated for both the left and right reference marks 111, 113 and is applied to shift the reference marks 111, 113 to their true locations. Other points appearing on the two stereoscopic X-ray images 108, 110 may now be digitized relative to the two reference marks 111, 113. In summary, a mathematical translation is performed to locate the left reference mark 111 at X=0, Y=0. A mathematical rotation is then performed to bring the right reference mark 113 to location Y=0. Parallax errors are subtracted to determine the true locations of the reference marks 111, 113 so that a point between them can be located. This point arbitrarily becomes location 0,0 of the two stereoscopic X-ray images 108, 110. Subsequently, any digitized point on the two stereoscopic X-ray images 108, 110 is manipulated by the transformation matrix to produce the X and Y coordinates of that point relative to location 0,0 on the images. Thereby, the raw digitizer coordinates are transformed into film coordinates.

After digitizing the point of interest 109 shown on the two stereoscopic X-ray images 108, 110 of the patient's breast, the coordinates of the endpoints of two lines are known. These lines are the two rays that began at the focal point of the X-ray, travelled through the patient's breast, and ended on the surface of the X-ray film. The equation for the intersection of these lines must then be solved. Since the endpoints of these two lines are measured with respect to the same reference, the point of intersection in X, Y, Z space is determined analytically using standard principles of analytical geometry. In accordance with well known principles of analytical geometry, X, Y, Z space is understood to represent an orthogonal coordinate system in which X is a horizontal coordinate, Y a vertical coordinate, and Z a coordinate perpendicular to both the X and Y coordinates.

Puncture instrument 32 of FIG. 1A provides horizontal angle, vertical angle, and insertion depth control of biopsy needle 34 mounted therein. The location of the rotational isocenter of puncture instrument 32 is known in the X, Y, and Z directions. It is therefore easy to "draw" a line between this rotational isocenter or pivot point and the point of interest 109 shown on the two stereoscopic X-ray images 108, 110. The projection of this line in the X-Z plane is the horizontal coordinate. The other coordinate is vertical and is obtained from the projection of this line in the Y-Z plane, with the exception that the biopsy needle does not radiate from the pivot point. The angle between the horizontal and vertical coordinates is known as the beta angle. Since the distance that the axis of the biopsy needle 34 is offset from from the pivot point is known, a right triangle can be "drawn" using the Y-Z projection and the amount of the needle offset. The third side of this right triangle represents the total distance to the point of interest 109 shown on the two stereoscopic X-ray images 108, 110 of the patient's breast and is used to set the depth to which biopsy needle 34 is to be inserted into the breast to locate the point of interest 109. The angle between the third side of the right triangle and the Y-Z projection is subtracted from the angle beta to determine the elevation or vertical angle. Alternatively, the axis of biopsy needle 34 could be positioned in the same plane as that of the pivot point to avoid the calculations required to take into account any offset distance between the axis of the biopsy needle 34 and the pivot point. The determinations of horizontal and vertical angles are subject to a final correction to account for slight angular errors in aligning the positioners for puncture instrument 32. The determined depth setting takes into account the length of the biopsy needle 34 and of the needle holder of puncture instrument 32.

Figure 5:
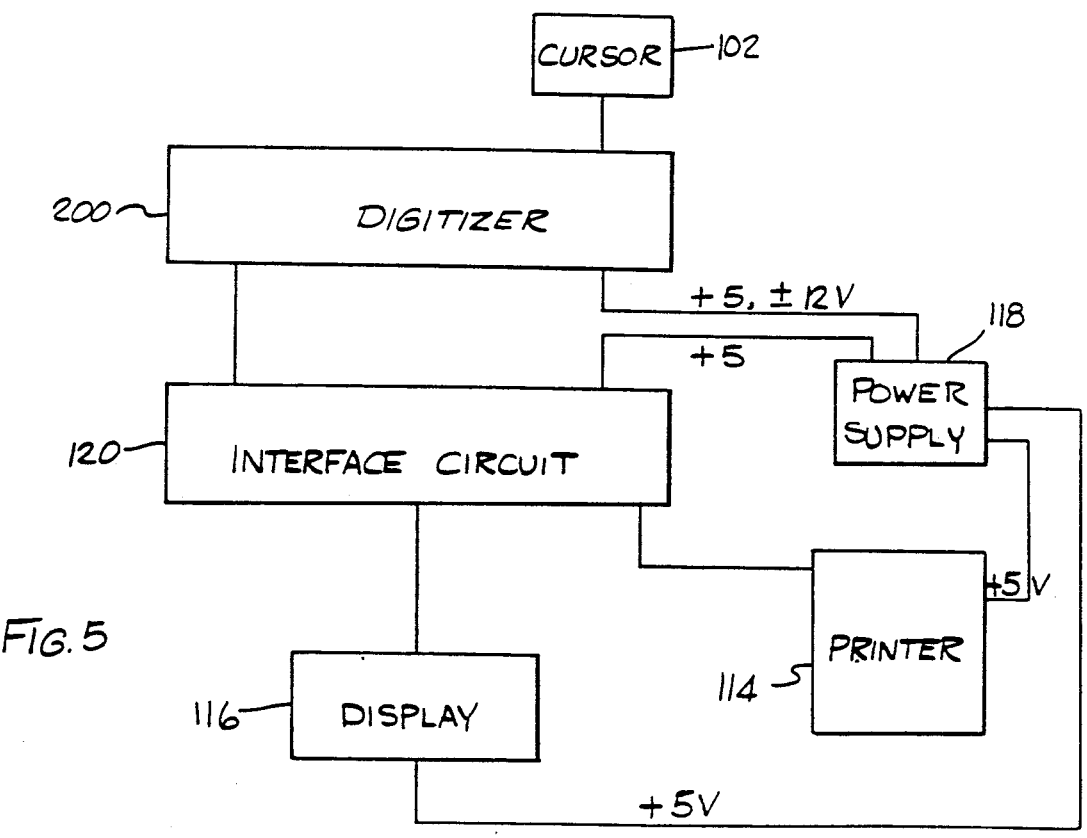
FIG. 5 is an electrical block diagram of the computer-digitizer console and cursor of FIG. 4.

Referring now to FIG. 5, there is shown a hardware block diagram of computer-digitizer console 100 and cursor 102 of FIGS. 4 and 9. Digitizer 200 may comprise a Model 2200 digitizer manufactured by Numonics, Inc. Digitizer 200 includes a platen area 104 that is backlit for viewing two stereoscopic X-ray images 108, 110 of the patient's breast for purposes of digitizing a point of interest 109 depicted on the two stereoscopic X-ray images 108, 110. Cursor 102 may comprise, for example, a one-button mouse with crosshairs, also manufactured by Numonics, Inc. Alphanumeric information display 116 may comprise a flip 2×20 vacuum flourescent display manufactured by IEE. Printer 114 may comprise a Model STP211-192 printer and associated interface circuitry manufactured by Seiko. A conventional power supply 118 supplies +5, +12 and −12 volts to power digitizer 200, alphanumeric information display 116, printer 114, and a computer and digitizer interface circuit 120. Computer and digitizer interface circuit 120 comprises the circuitry shown in the detailed schematic diagram of FIGS. 8A-D.

Referring now to the detailed schematic circuit diagram of FIGS. 8A-D, computer and digitizer interface circuit 120 includes a central processing unit or CPU 122 that may comprise an off-the-shelf Intel 8031 microprocessor. A pair of PROMS 124, 126 that may each comprise a 32K×8 PROM such as the TI27256 serve to store the routines and subroutines of instructions detailed in the firmware listing that follows this specification. These routines and subroutines of instructions are executed by CPU 122 to calculate the vertical angle, horizontal angle, and insertion depth parameters necessary to direct biopsy needle 34 of FIG. 1 to a precise point of interest within a patient's breast. A random access memory or RAM 128 provides temporary storage of data and other information during execution by CPU 122 of the routines and subroutines of instructions stored in PROMS 124, 126. RAM 128 may comprise, for example, a Hitachi 62565 32K×8 RAM. A system clock 130 may comprise any of a number of commercially available clock chips, such as the Signetics PCF8573 real time clock chip. A non-volatile electrically erasable (EE) ROM 132, that may comprise a Xicor X2404 EE ROM, serves to store calibration data and setup and adjustment parameters relating to the particular mammographic needle biopsy system in which it resides. A line driver 134, that may comprise a National Semiconductor DS8921A RS422 line driver, serves to interface computer and digitizer interface circuit 120 to a conventional remote display (not illustrated) that may be positioned adjacent patient table 20 of FIG. 1 to permit the operator of the mammographic needle biopsy system to view two stereoscopic X-ray images of the patient's breast from his or her operating position. A memory decoder 136, that may comprise a Texas Instruments 74LS155 memory decoder chip, serves to provide operation logic for computer and digitizer interface circuit 120. A buffer 138, that may comprise a Texas Instruments 74LS245 buffer chip, and a connector 140 serve to interface computer and digitizer interface circuit 120 to alphanumeric information display 116 located in computer-digitizer console 100 of FIG. 4. Similarly, another buffer 142, that may comprise a Texas Instruments 74LS374 buffer chip, and a connector 144 serveto interface computer and digitizer interface circuit 120 to printer 114. Finally, a logic level converter 146, that may comprise a Maxim MAX232 TTL to RS232 logic level converter, serves to interface computer and digitizer interface circuit 120 to platen area 104 of computer-digitizer console 100 of FIG. 4.

Referring now to FIG. 9, the function control area 112 of platen area 104 includes a control function menu, the individual functions of which are selected using cursor 102. In order to select the DATA ENTRY function, for example, the crosshairs of cursor 102 are positioned over that selected function and the button on cursor 102 is clicked. A series of prompts displayed on alphanumeric information display 116 then requests information regarding the left reference mark 111, the right reference mark 113, and the point of interest 109 depicted on stereoscopic X-ray image 108. In response to these prompts, the operator aligns the crosshairs of cursor 102 over the left and right reference marks 111, 113, clicking the button of cursor 102 over each reference mark. The operator is then prompted to enter the corresponding information from stereoscopic X-ray image 108. When this process has been completed, the message DATA ENTRY COMPLETED is displayed on alphanumeric information display 116.

The SELECT NEEDLE function shown on function control area 112 allows the operator to choose the appropriate biopsy needle for specific depth calculations. Several localizations on a single point of interest 109 may be performed using biopsy needles of different lengths by alternately selecting the SELECT NEEDLE and CALCULATE TARGET functions. Selecting the SELECT NEEDLE function cycles through five choices of biopsy needles.

The CALCULATE TARGET functin shown on function control area 112 initiates automatic computation by computer-digitizer console 100 of the vertical angle, horizontal angle, and insertion depth parameters defining point of interest 109. These results are then displayed on alphanumeric information display 116 and remain displayed until the button of cursor 102 is clicked to select another function.

The PRINT DATA function shown on function control area 112 initiates printing of the calculatd values of the vertical angle, horizontal angle, and insertion depth parameters on printer 114.

The ADVANCE PAPER function shown on function control area 112 advances the paper on printer 114 for the period of time during which the button on cursor 102 is depressed.

The BACK UP function shown on function control area 112 allows the operator to reenter the previous item of data during a data entry sequence.

The CANCEL function shown on function control area 112 cancels the present operation being performed by computer-digitizer console 100 and returns the system to an idle mode.

Computer-digitizer 100 is also operative for displaying a number of error codes on alphanumeric information display 116. The WRONG ORDER FOR IMAGE POINTS error code is displayed when the operator attempts to enter data via cursor 102 from stereoscopic X-ray image 110 before entering the appropriate data from stereoscopic X-ray image 108.

The BAD ORIENTATION OF FILM FOR DIGITIZING error code is displayed when either of the two stereoscopic X-ray images 108, 110 is mounted on digitizer viewing area 106 in a position such that reference marks 111, 113 are rotated more than 45 degrees from the X axis.

The REF MARKS MORE THAN 2.0 MM OFF error code is displayed when an error has been made in locating the reference marks 111, 113 on either of the two stereoscopic X-ray images 108, 110 using cursor 102.

The OVERFLOW IN MATH ROUTINES error code is displayed in the case of an internal program execution error and should never be observed.

The NOT ALL DATA POINTS TAKEN error code is displayed when the operator omits one of the six points of data depicted on the two stereoscopic X-ray images 108, 110 during the data entry operation. When this error code appears, the operator must re-initiate the data entry sequence using the DATA ENTRY function shown on function control area 112.

Other system error codes are displayed from time to time to indicate hardware problems within computer-digitizer console 100. For example, the ERROR READING TIME & DATE CLOCK, the ERROR WRITING TIME & DATE CLOCK, and the ERROR VERIFYING TIME & DATE CLOCK error codes are displayed whenever there is a hardware problem with the real time clock 130. The ERROR READING EEPROM and ERROR WRITING EEPROM error codes are displayed whenever there is a problem with the non-volatile set-up memory EEPROM 132. The BAD EEPROM CHECKSUM-DEFAULTS LOADED error code is displayed whenever a problem is detected with a checksum calculation that occurs when data is written to the EEPROM. When this error occurs, default data is automatically used to operate the system, which may result in a calibration error. The PRINTER BUSY TIME-OUT ERROR error code is displayed to indicate that printer 114 did not respond to the last character sent to it. Finally, the DEFAULT CALIBRATION DATA LOADED error code is displayed whenever default calibration data is used rather than calibration data from the non-volatile set-up memory EEPROM 132. When this occurs, the system must be re-calibrated by a qualified technician.

As stated in detail hereinabove, the mammographic needle biopsy system of the present invention function in accordance with the principle that a tumor which is photographed by X-ray from separate angles relative to the normal of the film plane is projected in different positions on the X-ray film. The coordinates of these projections can then be measured in relation to a pair of crosshairs projected onto the film as the X-ray photographs are being taken. By using standard analytical geometry relationships, the position of the tumor can be calculated very precisely. A puncture instrument is then used to position the tip of a hollow biopsy needle at the center of the tumor, thereby allowing the operator to extract a sample of the tumorous tissue. This procedure can be performed with an accuracy of better than 1.0 mm. Although the system of the present invention recognizes coordinates of the suspected tumor as X, Y, and Z values it translates these coordinates to vertical angle, horizontal angle, and insertion depth parameter values prior to their being visually displayed or printed for the operator.

The following is a listing of routines and subroutines of instructions executed by computer-digitizer console 100 of FIG. 5 to digitize an identified point of interest 109 depicted on two stereoscopic X-ray film images 108, 110 of a patient's breast, to compute the vertical angle, horizontal angle, and needle insertion depth parameters definging the point of interest 109, and to display those computed parameter to the operator.

We claim:

1. A precision mammographic needle biopsy apparatus comprising:

table means for supporting a female patient in a prone position, the table means comprising a head portion having a breast aperture therein through which one of the patient's breasts is permitted to pendulantly protrude for examination, the table means further comprising a foot portion hingedly attached to the head portion and arranged for gradual motion between a depending mounting and dismounting position and a position of substantial alignment with the head portion;

pedestal means supporting the table means, the pedestal means including motor control means for controllably raising and lowering the table means and for controllably, gradually moving the foot portion of the table means between the depending mounting and dismounting position and the position of substantial alignment with the head portion of the table means to facilitate mounting from a standing position and dismounting to a standing position by the patient, the motor control means being further operative for selectively tilting the table means, film holder arm, and X-ray arm in concert with respect to a horizontal plane;

a film holder arm pivotally mounted to the pedestal means, the film holder arm supporting an X-ray film holder, a compression paddle for compressing the patient's pendulant breast into a mammographic position, and a puncture instrument for controllably retaining a biopsy needle; and an X-ray arm pivotally mounted to the pedestal means in vertical alignment with the film holder arm, the X-ray arm supporting X-ray means for directing an X-ray beam in alignment with the patient's compressed pendulant breast for impingement onto an X-ray film retained in the X-ray film holder to thereby produce an X-ray film image of the patient's compressed pendulant breast.

2. A precision mammographic needle biopsy apparatus as in claim 1 wherein a patient receiving surface of the table means is generally concave with respect to a longitudinal axis of the table means.

3. A precision mammographic needle biopsy apparatus as in claim 1 wherein an area surrounding the breast aperture in the table means is dish-shaped to permit examination of a portion of the patient's breast that is immediately adjacent her chest wall.

4. A precision mammographic needle biopsy apparatus as in claim 1, further comprising adjustable diaphragm means, rotatable within the breast aperture, for covering a selected portion of the breast aperture to prevent the one of the patient's breasts not under examination from protruding at all through the breast aperture, while at the same time permitting the one of the patient's breasts under examination to completely protrude through the breast aperture.

5. A precision mammographic needle biopsy apparatus as in claim 1, further comprising compression plate means supported on the film holder arm in a spaced relationship in front the X-ray film holder, the compression plate means cooperating with the compression paddle to compress the patient's breast under examination into the mammographic position in a spaced relationship in front of the film holder to thereby magnify the X-ray film image of the patient's compressed pendulant breast under examination.

6. A precision mammographic needle biopsy apparatus as in claim 1 further comprising a spring loaded biopsy gun controllably retained by said puncture instrument and operative for rapid insertion of the biopsy needle to an identified point of interest within the patient's compressed pendulant breast.

7. A precision mammographic needle biopsy apparatus as in claim 1 wherein said puncture instrument includes a first means for permitting pivotal motion of the biopsy needle about a vertical pivoting axis, and a second means for permitting pivotal motion of the biopsy needle about a horizontal pivoting axis, said biopsy needle being retained with the puncture instrument in a position such that the biopsy needle lies in a plane common with a plane in which the horizontal pivoting axis lies.

8. A precision mammographic needle biopsy apparatus comprising:

table means for supporting a female patient in a prone position, the table means having a breast aperture therein through which one of the patient's breasts is permitted to pendulantly protrude for examination;

pedestal means supporting the table means, the pedestal means including motor control means for controllably raising and lowering the table means;

a film holder arm supporting an X-ray film holder, a compression paddle for compressing the patient's pendulant breast into a mammographic position, and a puncture instrument for controllably retaining a biopsy needle;

first tapered roller bearing means cooperatively coupling the film holder arm to the pedestal means for permitting radial motion of the film holder arm in a first horizontal plane;

an X-ray arm supporting X-ray means for directing an X-ray beam in alignment with the patient's compressed pendulant breast for impingement onto an X-ray film retained in the X-ray film holder to thereby produce an X-ray film image of the patient's compressed pendulant breast under examination; and second tapered roller bearing means vertically aligned with the first tapered roller bearing means and cooperatively coupling the X-ray arm to the pedestal means for permitting radial motion of the X-ray arm in a second horizontal plane.

9. A precision mammographic needle biopsy apparatus as in claim 8, further comprising:

a circular detent plate rotationally mounted in vertical alignment with the first and second tapered roller bearing means, the circular detent plate having a plurality of wedge-shaped detents spaced along the periphery thereof;

arm lock means mounted to the pedestal means for selectively locking radial motion of the film holder arm and X-ray arm with respect to the pedestal means, the arm lock means including a first spring-loaded locking lever having a wedge-shaped lock tab at one end thereof adapted for mating engagement with a selected one of the plurality of wedge-shaped detents spaced along the periphery of the circular detent plate, the first spring-loaded locking lever having a wedge-shaped opening at a pivot end thereof adapted for engagement with a fixed pivot pin; and X-ray arm lock means mounted to the pedestal means for selectively locking radial motion of the X-ray arm with respect to the film holder arm, the X-ray arm lock means including a second spring-loaded locking lever having a wedge-shaped lock tab at one end thereof adapted for mating engagement with a different selected one of the plurality of wedge-shaped detents spaced along the periphery of the circular detent planted, the second spring-loaded locking lever having a wedge-shaped opening at a pivot end thereof adapted for engagement with a fixed pivot pin.

10. A precision mammographic needle biopsy apparatus as in claim 8 further comprising a spring loaded biopsy gun controllably retained by said puncture instrument and operative for rapid insertion of the biopsy needle to an identified point of interest within the patient's compressed pendulant breast, 11. A precision mammographic needle biopsy apparatus as in claim 8 wherein said puncture instrument includes a first means for permitting pivotal motion of the biopsy needle about a vertical pivoting axis, and a second means for permitting pivotal motion of the biopsy needle about a horizontal pivoting axis, said biopsy needle being retained within the puncture instrument in a position such that the biopsy needle lies in a plane common with a plane in which the horizontal pivoting axis lies.

12. A precision mammographic needle biopsy apparatus comprising:

table means for supporting a female patient in a prone position, the table means having a breast aperture therein through which one of the patient's breasts is permitted to pendulantly protrude for examination;

pedestal means supporting the table means, the pedestal means including motor control means for controllably raising and lowering the table means;

a film holder arm pivotally mounted to the pedestal means for horizontal radial motion, the film holder arm supporting an X-ray film holder, a compression paddle for compressing the patient's pendulant breast into a mammographic position, and a puncture instrument for controllably retaining a biopsy needle;

an X-ray arm pivotally mounted to the pedestal means in vertical alignment with the film holder arm, the X-ray arm adapted for horizontal radial motion and for supporting X-ray means for directing a first X-ray beam in alignment with the patient's compressed pendulant breast for impingement onto an X-ray film retained in the X-ray film holder when the X-ray arm is in a first position relative to a plane of the X-ray film and for directing a second X-ray beam in alignment with the patient's compressed pendulant breast for impingement onto the X-ray film when the X-ray arm is in a second position relative to the plane of the X-ray film to thereby produce first and second stereoscopic X-ray film images of the patient's compressed pendulant breast under examination;

means for projecting aligned left and right reference marks onto the first and second stereoscopic X-ray film images; and computer-digitizer means, including a digitizer platen/light box viewing surface and digitizer cursor means, the digitizer platen/light box viewing surface being operative for receiving the first and second stereoscopic X-ray film images of the patient's compressed pendulant breast and for permitting the operator to view those first and second stereoscopic X-ray film images to identify a point of interest within the patient's compressed pendulant breast depicted in each of the first and second stereoscopic X-ray film images, the computer-digitizer means being thereafter operative for digitizing, in response to actuation of the digitizer cursor means when sequentially positioned over the left and right reference marks and the identified point of interest depicted on the first and second stereoscopic X-ray film images, the identified point of interest with respect to the aligned left and right reference marks, the computer-digitzer means being further operative for automatically computing the spatial coordinates of the identified point of interest in terms of vertical angle, horizontal angle, and insertion depth parameters relative to insertion of the biopsy needle to the identified point of interest, and for visually displaying those computed spatial coordinates of the identified point of interest to the operator.

13. A precision mammographic needle biopsy apparatus as in claim 12 further comprising a spring-loaded biopsy gun controllably retained by the puncture instrument and operative for rapid insertion of the biopsy needle to the identified point of interest within the patient's compressed pendulant breast.

14. A precision mammographic needle biopsy apparatus as in claim 12 wherein the puncture instrument further comprises horizontal angle control means, vertical angle control means, needle insertion depth control means, and motorized position encoder means coupled to the computer-digitizer means and responsive to computation thereby of the horizontal angle, vertical angle, and insertion depth parameters, for positioning the biopsy needle in correspondence with the computed verticle angle and horizontal angle parameters and for thereafter automatically inserting the biopsy needle into the patient's compressed pendulant breast a distance corresponding to the computed insertion depth parameter to thereby position a tip of the biopsy needle at the identified point of interest within the patient's compressed pendulant breast.

15. A precision mammographic needle biopsy apparatus as in claim 14 further comprising a spring-loaded biopsy gun controllably retained by the puncture instrument and operative for rapid insertion of the biopsy needle to the identified point of interest within the patient's compressed pendulant breast.

16. A precision mammographic needle biopsy apparatus as in claim 12 wherein said puncture instrument includes a first means for permitting pivotal motion of the biopsy needle about a vertical pivoting axis, and a second means for permitting pivotal motion of the biopsy needle about a horizontal pivoting axis, said biopsy needle being retained within the puncture instrument in a position such that the biopsy needle lies in a plane common with a plane in which the horizontal pivoting axis lies.

* * * * *